(12) United States Patent
Nakajima et al.

(10) Patent No.: US 6,559,794 B1
(45) Date of Patent: May 6, 2003

(54) POSITION DETERMINING SYSTEM, RECEIVING SYSTEM METHOD OF DETERMINING THE POSITION OF A MOVABLE OBJECT AND METHOD OF RECEIVING DATA REGARDING THE POSITION

(75) Inventors: Syuji Nakajima, Kunitachi (JP); Hiroyuki Chubachi, Ome (JP); Makoto Nakagawa, Hamura (JP); Nobuhiro Aoki, Kokubunji (JP); Kazuto Ushiyama, Machida (JP); Satoshi Yoshiike, Ome (JP)

(73) Assignee: Casio Computer Co., Ltd., Tokyo (JP)

( * ) Notice: Subject to any disclaimer, the term of this patent is extended or adjusted under 35 U.S.C. 154(b) by 0 days.

(21) Appl. No.: 09/473,524

(22) Filed: Dec. 28, 1999

(30) Foreign Application Priority Data

Dec. 31, 1998 (JP) .......................................... 10-377621

(51) Int. Cl.[7] .............................................. H04B 7/185
(52) U.S. Cl. ............................ 342/357.06; 342/357.01; 701/207; 701/215
(58) Field of Search ................................ 701/201, 207, 701/208, 214, 215; 342/357.01, 357.06, 357.12, 357.13; 455/12.1, 13.2

(56) References Cited

U.S. PATENT DOCUMENTS 6,111,540 A * 8/2000 Krasner .................... 342/357.1
6,167,346 A * 12/2000 Fukawa ...................... 701/208
6,266,042 B1 * 7/2001 Aratani ....................... 345/132

FOREIGN PATENT DOCUMENTS

| JP | 05-306940 | 11/1993 |
| JP | 07-209405 | 8/1995 |
| JP | 2715695 | 11/1997 |
| JP | 2849750 | 11/1998 |

* cited by examiner

Primary Examiner—Gertrude Arthur
(74) Attorney, Agent, or Firm—Frishauf, Holtz, Goodman & Chick, P.C.

(57) ABSTRACT

A position determining system, a receiving system, a method of determining the position of a movable object and a method of receiving data regarding the position of the movable object are provided. The position determining system comprise a position determining unit, a display unit and a controller. The position determining unit determines the position of a movable object based on position information sent from GPS satellites. The display unit displays the position of the movable object which has been determined by the position determining unit. The controller controls a time interval at which the position of the movable object is determined by said position determining unit, in accordance with a degree of position change occurring in the position to be displayed on the display unit. Accordingly, in the position determining system, elimination of consumption power can be realized in a position determination process which is not necessarily performed, while the system is advantageously handled.

13 Claims, 12 Drawing Sheets

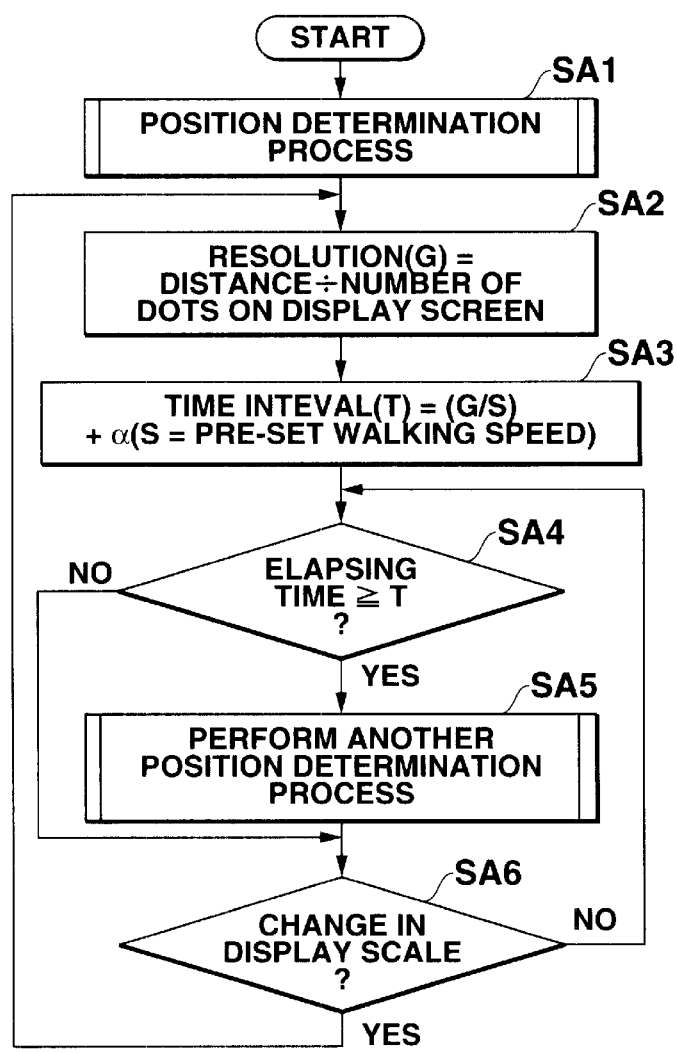

| DISPLAY REDUCED SCALE (Km) | TIME INTERVAL FOR POSITION DETERMINATION (MIN) |
|---|---|
| 0 ~0.5 | 1 |
| 0.5 ~1 | 2 |
| 1 ~5 | 10 |
| 5 ~10 | 20 |
| 20 ~ | 40 |

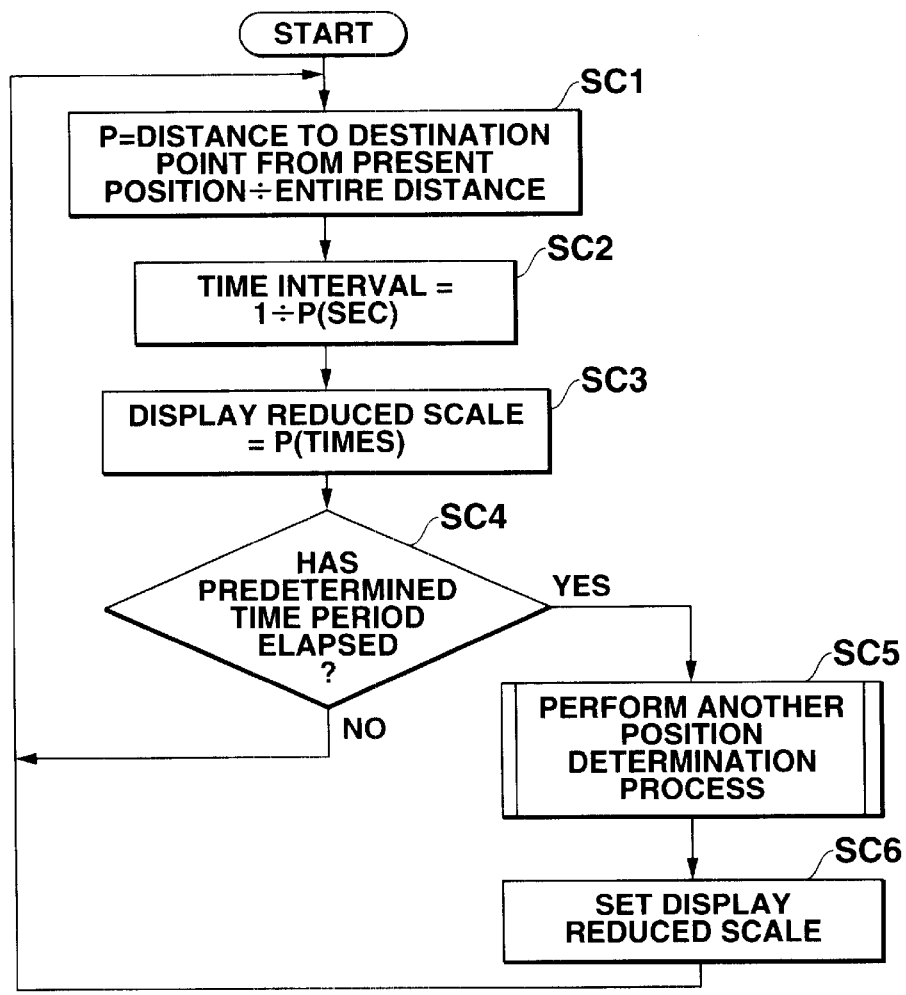

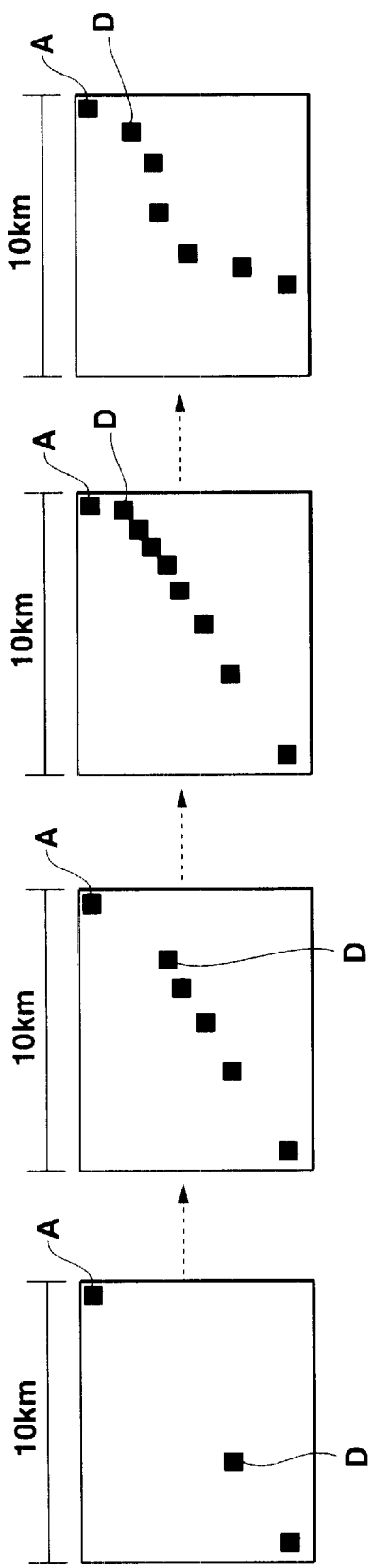

□ DEPARTURE POINT   ▨ PRESENT POSITION   ■ DESTINATION POINT

| TRAVELING SPEED (Km/h) | TIME INTERVAL FOR POSITION DETERMINATION (SEC) |
|---|---|
| 0 ~5 | X = 600 |
| 5 ~10 | X = 120 |
| 10 ~15 | X = 60 |
| 15 ~20 | X = 30 |
| 20 ~25 | X = 10 |
| 25 ~30 | X = 5 |
| 30 ~ | X = 1 |

POSITION DETERMINING SYSTEM, RECEIVING SYSTEM METHOD OF DETERMINING THE POSITION OF A MOVABLE OBJECT AND METHOD OF RECEIVING DATA REGARDING THE POSITION

FIELD OF THE INVENTION

The present invention relates to a portable-type position determining system and a receiving system, and more particularly to a position determining system and a receiving system capable of receiving GPS electric waves which are sent from GPS (Global Positioning System) satellites.

BACKGROUND OF THE INVENTION

Description of the Related Art

Conventionally, a position determining system which uses information sent from GPS satellites and which is held by a movable object, such as a user, etc. determines the position of the movable object, by receiving information regarding the determined positions. The information regarding the determined positions are navigation signals, such as ephemeris data, almanac data, etc. The ephemeris data are orbital information representing orbit into which a satellite is put or correction information used for time correction. The almanac data are schematic orbit information representing the entire satellites. To receive data from the respective GPS satellites, it is necessary that a timing of sending data from the respective satellites coincides with a timing of receiving such data. The timing of sending data at all times varies, since the GPS satellites or the position determining systems at all times shift from place to place. Therefore, in car navigation systems using the GPS, the timing of sending data from the satellites at all times coincides with the timing of receiving such data, thereby a position determination process can continuously be performed.

However, if the same position determination process as that performed in car navigation systems is performed in a position determining system which is of a battery-powered wristwatch type and of a portable type, a drawback arises in that the battery life of such a small-size position determining system is expected short. For the purpose overcoming the above drawback, the large volume of battery may be employed, resulting in another problem that the small-size position determining system is manufactured large in size.

SUMMARY OF THE INVENTION

Accordingly, the present invention has been made in consideration of the above, and an object thereof is to provide a position determining system, a receiving system, a method of determining the position of a movable object and a method of receiving data regarding the position, wherein unnecessary position determination processes are eliminated.

Another object of the present invention is to provide a position determining system, a receiving system, a method of determining the position of a movable object and a method of receiving data regarding the position, which appropriately achieve a reduction in power consumption.

According to one aspect of this invention, there is provided a position determining system comprising:

a receiver which receives position information sent from GPS satellites;

a position determining unit which determines a position of the receiver based on the position information received by the receiver;

a display unit which displays the position of the receiver which is determined by the position determining unit; and a controller which controls a time interval at which the position of the receiver is determined by the position determining unit, in accordance with a resolution of an area between predetermined positions displayed on the display unit.

In this structure, in a state where the determined position is not displayed on the display unit, the position determining unit is not required to perform unnecessary position determination processes.

According to another aspect of this invention, there is provided a position determining system comprising:

a receiver which receives position information sent from GPS satellites;

a position determining unit which determines a position of the receiver based on the position information received by said receiver;

a display unit which displays the position of the receiver which is determined by said position determining unit; and a controller which controls a time interval at which the position of the receiver is determined by said position determining unit, based on a reduced scale of a display screen on which the position of the receiver is displayed.

According to another aspect of this invention, there is provided a position determining system comprising:

a receiver which receives plural pieces of position information which are sent from a plurality of GPS satellites;

a position determining unit which determines a position of a movable object based on the plural pieces of position information which are received by the receiver; and a controller which determines an appropriate number of GPS satellites from the plurality of GPS satellites which send the plural pieces of position information to be received by the receiver. In the structure, a desired number of GSP satellites are set when the position determining unit determines the position of the movable object. Thereby, the electric power to be consumed by the receiver when determining its own position can be eliminated.

According to still another aspect of this invention, there is provided a receiving system comprising:

a receiver which receives position information sent from GPS satellites;

a position determining unit which determines a position of the receiver based on the position information received by the receiver; and a controller which controls an interval at which the position determining unit determines the position of the receiver, in accordance with an output of a power source which supplies electrical power to the receiver and the position determining unit. In such a structure, the load onto the receiver may become light in accordance with the remaining battery.

According to yet still another aspect of this invention, there is provided a receiving system comprising:

a receiver which receives position information sent from GPS satellites;

a position determining unit which determines a position of the receiver based on the position information received by the receiver; and a controller which turns off a power supply to the receiver and the position determining unit when a predetermined time period lapses after the position determining unit determines the position of the receiver. In this structure, immediately after the receiver receives the position information, the electric power to the receiver is broken, thereby saving the consumption power.

According to a further aspect of this invention, there is provided a receiving system comprising:

a receiver which receives plural pieces of position information which are sent from a plurality of GPS satellites;

a position determining unit which determines a position of a movable object based on the plural pieces of position information received by the receiver;

a storage unit which stores calculation data regarding leap seconds which are necessary for correcting a satellite time sent from the plurality of GPS satellites. In such a structure, the receiver may not receive the calculation data regarding the leap seconds, thereby saving the consumption power.

According to a still further aspect of this invention, there is provided a method comprising:

receiving position information sent from a plurality of GPS satellites;

determining a position based the received position information; and controlling a time interval, at which the position is determined, in accordance with the determined position. With this method, in a state where the determined position is not displayed by the displaying step, unnecessary position determination processes are not performed by the position determining step.

According to a yet still further aspect of this invention, there is provided a method comprising:

receiving position information sent from a plurality of GPS satellites;

determining a position based on the received position information; and determining an appropriate number of GPS satellites from the plurality of GPS satellites which send the position information to be received. With this method, the predetermined number of GPS satellites are set. Therefore, the receiving step may not perform unnecessary position determination processes during the time the position of the movable object is determined.

Broadly defined, the present invention provides a position determining system comprising:

a receiver which receives position information sent from GPS satellites;

a position determining unit which determines a position of the receiver based on the position information received by said receiver; and a controller which controls a time interval at which the position of the receiver is determined by said position determining unit, in accordance with the detected position.

BRIEF DESCRIPTION OF THE DRAWINGS

These objects and other objects and advantages of the present invention will become more apparent upon reading of the following detailed description and the accompanying drawings in which:

FIG. 2 is a diagram showing memory areas in an RAM;

FIG. 3 is a flowchart for explaining a position determination process performed by the position determining system being in GPS mode;

FIG. 8 is a diagram showing a time interval setting table according to the third embodiment of the present invention;

FIGS. 9A to 9D are diagrams each exemplifying a navigation image to be displayed on a display screen;

FIG. 10 is a flowchart for explaining a position determination process performed by the position determining system, being in GPS mode, according to the fourth embodiment of the present invention;

DETAILED DESCRIPTION OF THE PREFERRED EMBODIMENTS

First Embodiment

The first embodiment of the present invention will now be explained with reference to the accompanying drawings.

Figure 1A:
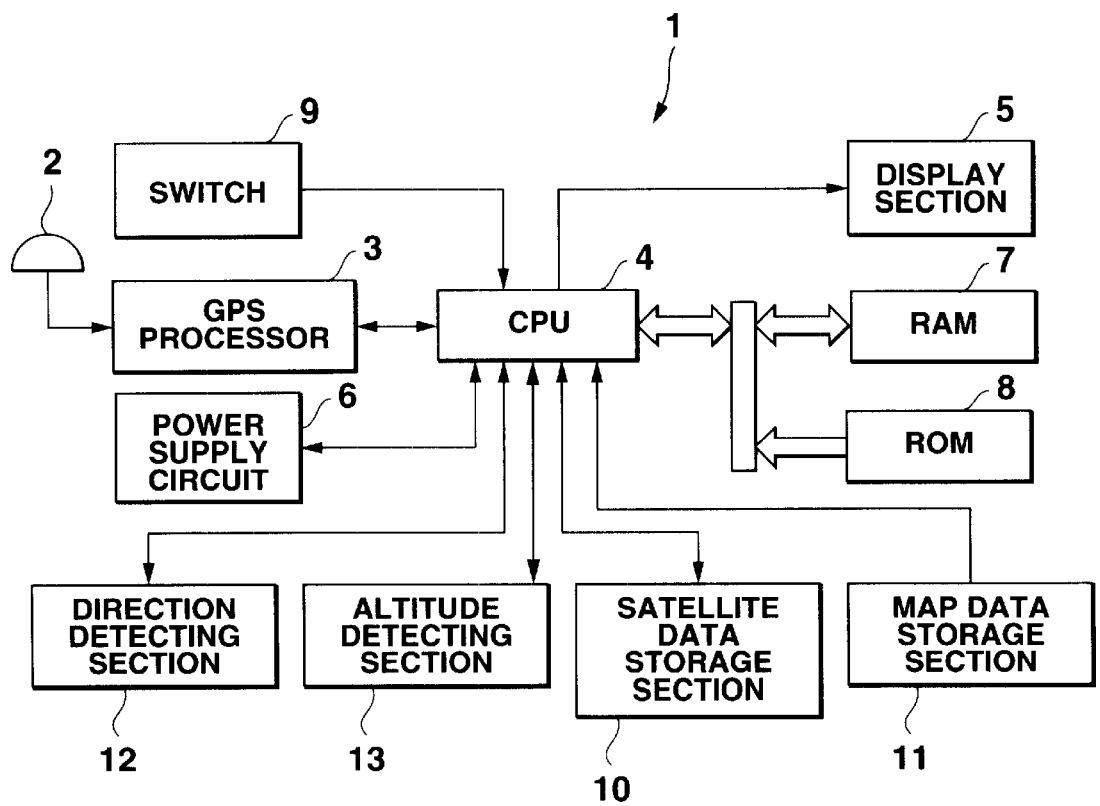
FIG. 1A is a diagram showing a position determining system according to the first embodiment of the present invention.

FIG. 1A is a block diagram showing a position determining system 1 according to the present invention. Let it be assumed that the position determining system 1 of this embodiment is of a battery-powered wristwatch type. The position determining system 1 is held by a movable object, etc., such as a user or the like, and determines the position of the system which is moved together with the movable object.

The position determining system 1 of this embodiment comprises a GPS antenna 2, a GPS processor 3, a CPU 4, a display section 5, a power supply circuit 6, a RAM 7, a ROM 8, a switch 9, a satellite data storage section 10, a map data storage section 11, a direction detecting section 12 and an altitude detecting section 13.

In the position determining system 1, the GPS antenna 2 receives radio waves in the L1 band from GPS satellites, and sends the received radio waves to the GPS processor 3. The GPS processor 3 is composed of an RF (radio frequency) receiver, an A/D (analog/digital) converter, a data register, a counter, a decoder, a CPU controlling all of the above, a ROM, a RAM, and the like. The GPS processor 3 amplifies and demodulate the received radio waves, thereafter reading satellite data, such as ephemeris or almanac data. Then, the GPS processor 3 calculates, that is, determines its own position based on the received the read data. The ephemeris data may be stored in the RAM 7 or the satellite data storage section 10 beforehand, while the almanac data may be stored in the data storage section 10.

The data regarding the determined position which has been calculated by the GPS processor 3 is sent to the CPU 4, which entirely controls the position determining system 1, and is displayed on a small-size display unit such as an LCD or the like, which is mounted in the display section 5. The display unit is of a dot matrix type, and is capable of displaying a navigation image (refer to FIGS. 4 and 5) expressing a departure point A, a destination point B, a waypoint C, a present position D, etc., by one or more dots.

When no position determination is performed, the display unit displays the present time, etc., which has been sent from a non-illustrative watch to the CPU 4.

Figure 1B:
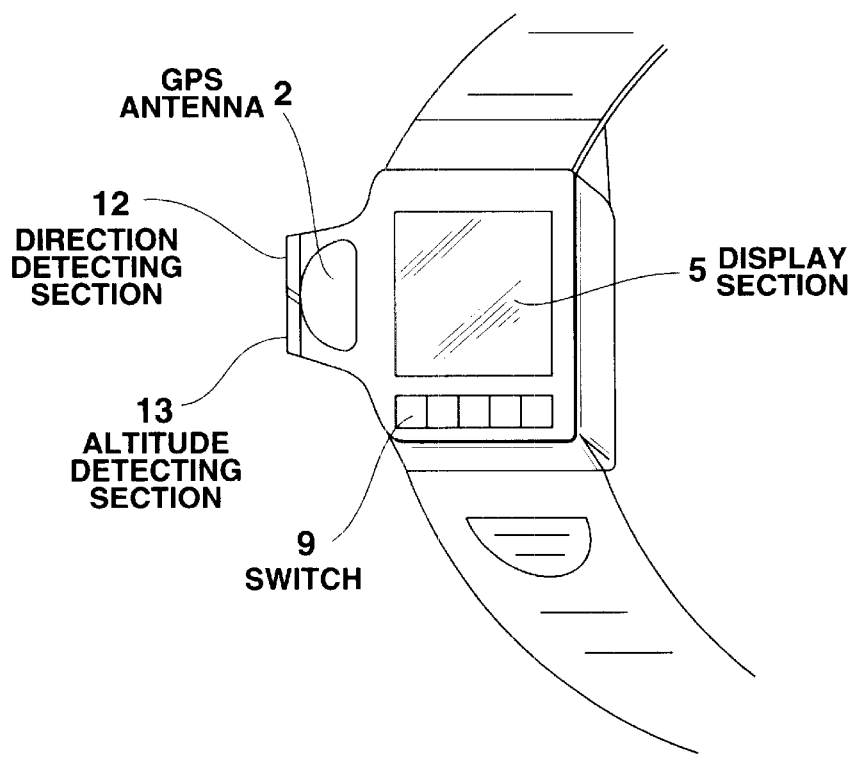
FIG. 1B is a diagram showing an exterior view of the position determining system according to the first embodiment of the present invention.

FIG. 1B illustrates an exterior view of the wristwatch-type position determining system 1. A user of such a wristwatch may perform operations through the switch 9. The display section 5 displays various data, such as the present time, navigation images, etc.

The power supply circuit 6 including a power supply supplies electric power to the GPS processor 3 and the CPU 4. The RAM 7 serves as a working memory. The CPU 4 is operated based on the programs stored in the ROM 8, and controls the GPS processor 3, the CPU 4, the power supply circuit 6 and the like.

As illustrated in FIG. 2, included in the RAM 7 is a memory area 7a containing time data A, regarding the time the previous position determination process has been performed, and time interval data B, regarding time intervals for position determination, both data of which are user in the following processes. The CPU 4 is connected to the switch 9, the satellite data storage section 10, the map data storage section 11, the direction detecting section 12 and the altitude detecting section 13. The switch 9 is connected to a plurality of switches and is used by the user of the wristwatch in order to operate the position determination system 1. The satellite data storage section 10 is a non-volatile memory, such as an EEPROM or the like, for storing the satellite data which is read or updated by the GPS processor 3 as needed. The map data storage section 11 is a ROM in which data not to be updated such as map data, position data are stored. The direction detecting section 12 is constituted of a sensor for detecting the direction and a processing circuit for processing a detected signal from the sensor, whereas the altitude detecting section 13 is constituted of a sensor for detecting the altitude and a processing circuit for processing a detected signal from the sensor.

Operations executed by the position determining system in GPS mode, as selected by the user, will now be explained with reference to the flowchart shown in FIG. 3. When the system enters the GPS mode, the GPS processor 3 estimates the present position of the position determining system. A navigation image for informing the user of the estimated data (the present position) is displayed on the display unit in a displayable reduced scale which has been set when the GPS mode of the position determining system is terminated (Step SA1).

Figure 4:
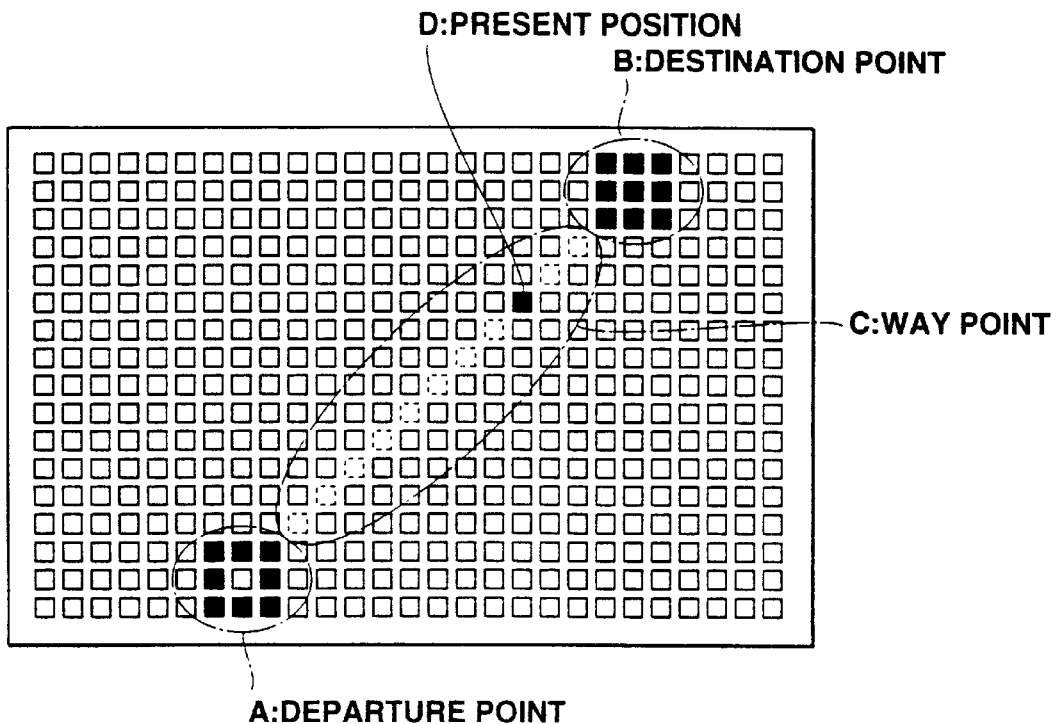
FIG. 4 is a diagram exemplifying a navigation image to be displayed on a display screen in the first embodiment.

FIG. 4 exemplifies the navigation image which is so displayed in a display reduced scale that the departure point A and the destination point B can be seen on one screen. The departure point A, the destination point B, the waypoint C, which connects the points A and B, and the present position D are displayed on the display screen.

In the position determination process for determining the present position, the present time at any determination point is stored as the time data A in the RAM 7. When the position determination process is completed, a resolution (G) of the display screen at the position-determined point is calculated. This calculation is performed on the basis of the distance, which has been estimated based on the map data, between given two points, such as the departure point A and the destination point B, and the number of dots on the display screen (Step SA2). The resolution (G) expresses the distance of a displayable area to be displayed on the screen with a single dot, that is, the minimum required distance for showing changes in the present position of the position determining system on the display screen. For example, when the estimated distance between the departure point A and the destination point B is 12 km, as shown in FIG. 4, the distance between the two is expressed with 12 dots on the display screen, therefore, the resolution (G) is 1 km.

Subsequently, in Step SA3, a time interval (T) for position determination is calculated based on the calculated resolution (G) and a pre-set walking speed (S). The calculated data is stored as the data B for position determination in RAM 7. When the user travels at the pre-set walking speed, the time interval for position determination (T) is a rough time, wherein an error ($\alpha$) is added to the minimum required time for the display screen to show the position of the user travelling. For example, the time interval for position determination (T) is ten minutes, when the user travels at the walking speed (S) of 100 m/min.

Afterwards, it is determined whether the elapsing time, which is calculated based on the time data, regarding the time the position determination has previously been performed, stored in the RAM 7 and the present time, is equal to or exceeds the time interval for position determination (T) (Step SA4). In Step SA4, when determined that the elapsing time is equal to or exceeds the time interval for position determination, another position determining process is performed (Step SA5). On the other hand, when determined that the elapsing time is not equal to or shorter than the time interval for position determination, the flow advances to Step SA6. In Step SA6, it is determined whether there is any change in the display reduced scale. When determined that no change is made in the display reduced scale, the flow goes back to Step SA4. Alternatively, when determined that a change is made in the display reduced scale, the flow returns back to Step SA2, in which the time interval for position determination (T) is calculated again.

Figure 5:
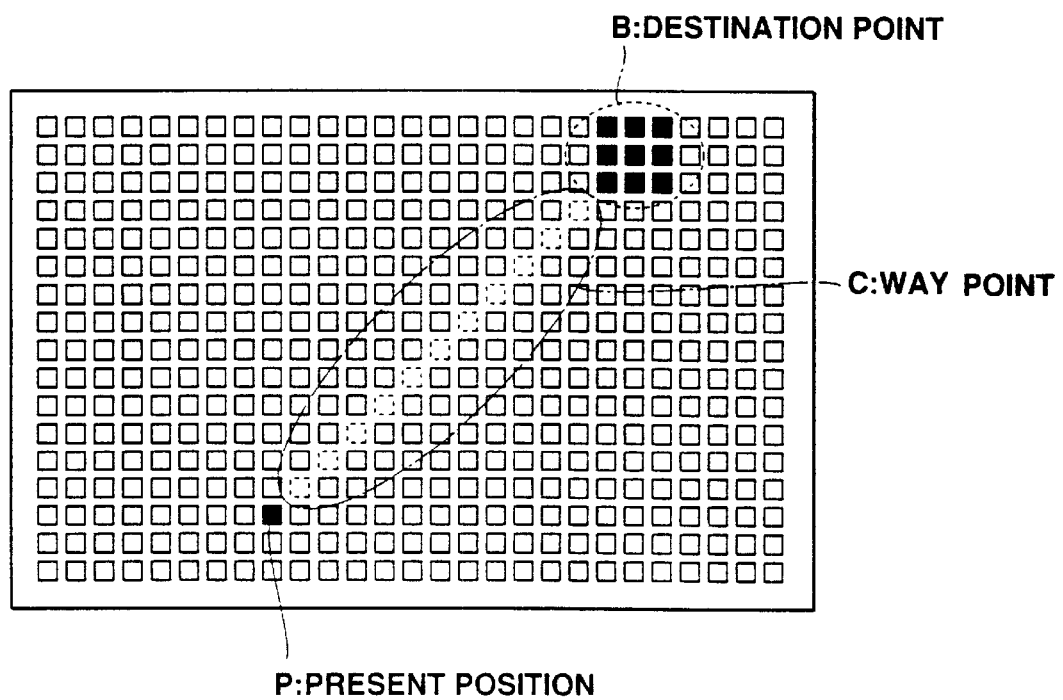
FIG. 5 is a diagram showing another navigation image displayed in a different reduced scale from that shown in FIG. 4.

For example, any change in the reduced scale can be made from that shown in FIG. 4 into a scale in which the present point D together with the destination point B are displayed as shown in FIG. 5. In this case, the resolution (G) becomes 250 m, thereby the time interval (T) is three minutes, and the estimated resolution (G) and the time interval (T) are stored in the RAM 7, that is, updated. Subsequently, the position of the position determining system is determined at intervals of the calculated time interval (T), that is, three minutes. If there is any change in the display reduced scale, the time interval (T) is recalculated. Then, the procedures from and following Step SA2 will be repeated until the GPS mode is terminated.

Accordingly, in a state where the calculated result regarding the position information and performed by the GPS processor 3 is unlikely to be displayed on the display screen, the GPS processor 3 is not required to perform any position determination processes which are not really necessary. Therefore, a long battery life of the position determining system can be expected, and the system can be manufactured in small size.

In this embodiment, the explanation has been made to the example, in which the time interval (T) for position determination has been calculated based on the resolution of the display screen and the pre-set walking speed. In such a case, the higher the resolution, the clearer the traveling (position change) of the user can be displayed. Therefore, when the resolution is low, the time interval for position determination is set longer, whereas the time interval is set shorter, when the resolution is high. Accordingly, the position determining system 1 of this invention can advantageously be realized, when changes are made in the time interval merely either linearly or non-linearly based on the resolution of the display screen.

Second Embodiment

The second embodiment of the present invention will now be explained. The position determining system of the second embodiment has the same structure as that shown in FIG. 1A.

Figures 6, 7:
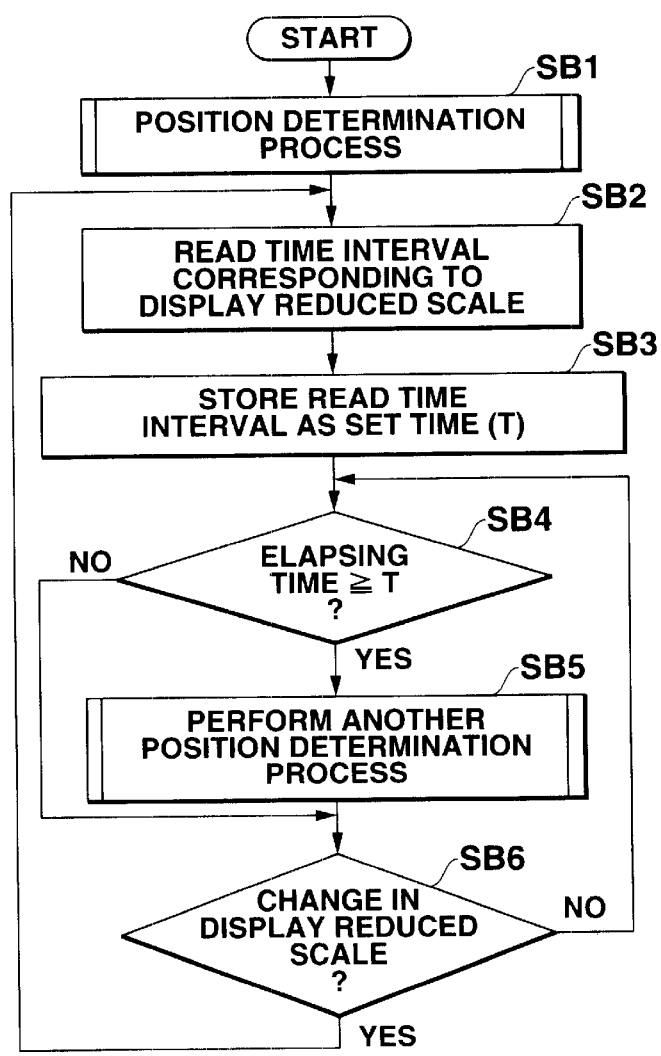
FIG. 6 is a diagram showing a time interval setting table according to the second embodiment of the present invention.
FIG. 7 is a flowchart for explaining a position determination process performed by the position determining system being in GPS mode.

As shown in FIG. 6, recorded in the ROM 8 are data forming a time interval setting table T1, in which a plurality of display reduced scales C and time intervals B for position determination are set in a manner corresponding with each other. To be more specific, each of the display reduced scales C represents the horizontal distance of a map showing the present position, the destination point and the way points. The shorter the distance, the shorter the time interval for position determination.

In this embodiment of the present invention having the above-described structure, procedures shown in the flowchart of FIG. 7 and performed by the position determining system in GPS mode, as selected by the user, will now be explained. When the position determining system is in GPS mode, as selected by the user, the GPS processor 3 performs a position determination process for determining its position (Step SB1). The GPS processor 3 then controls the display unit to display a navigation image for informing the user of the determined position (present position) in the display reduced scale, which has been set when the GPS mode was terminated previously.

The GPS processor 3 reads out the time interval corresponding to the reduced scale from the time interval setting table T1 (Step SB2), and stores the read data as a set time (T) in the RAM 7 (Step SB3). Subsequently, the GPS processor 3 performs the position determination process at intervals ("Yes" in Step SB4) which are set in the RAM 7 (Step SB5). During such a process, if it is determined that a change is made in the display reduced scale ("Yes" in Step SB6), a procedure for setting a new time interval corresponding to the display reduced scale after changed is repeated.

As the actual distance of the displayable area corresponding to the width of the display screen becomes longer, that is, as the travelling (position change) of the user is vaguely displayed, the time interval for position determination is set longer. Thus, the GPS processor 3 does not have to perform unnecessary processes for position determination in a state where the travelling (position change) of the user is not distinctly displayed. Therefore, the long battery life of the position determining system can be expected, and the system can be manufactured in small size.

In this embodiment of the present invention, it has been assumed that the display reduced scales are set nonlinearly. However, the display reduced scales can be set linearly. In such a case, the time interval for position determination can be changed in accordance with a change rate of the display reduced scales.

The display reduced scale and the resolution, as described in the first embodiment, are in an inseparable relation from each other and are equal to each other. Therefore, in a case where the area of the display screen is displayed on the display unit at the maximum area value, the position determining system of this embodiment can advantageously be realized as briefly explained in the first embodiment, in which the time interval for position determination is changed either linearly or nonlinearly simply based on the calculated resolution.

Third Embodiment

The third embodiment of the present invention will now be explained. In this embodiment, in the position determining system having the same structure as that shown in FIG. 1A, stored in the ROM 8 in advance are data forming a time interval setting table T2, shown in FIG. 8, containing a plurality of remaining distances D and time intervals B for position determination in a manner corresponding with each other. The plurality of remaining distances D and the time intervals B for position determination are set in such a way that as the remaining distance D becomes shorter, the time interval B for position determination is set shorter as well.

In this embodiment, when the position determining system 1 is in GPS mode, as selected by the user, the GPS processor 3 performs the position determination process, and controls the display unit to display a navigation image for informing the user of the calculated result (the present position). Subsequently, the GPS processor 3 calculates the distance from the present point to the destination point, that is, the remaining distance between the two points, based on the position information (latitude/longitude) regarding the present position and the destination point. Then, the GPS processor 3 retrieves the time interval B corresponding to the calculated result from the time interval setting table T2, stores the retrieved data in the RAM 7, and sets the retrieved time interval B as an interval between the present time and the time the next position determination process is performed. Every time the position determination process is performed, a process for re-setting the time interval between the present time and the time the next position determination is repeated. In every position determination process, the present point is plotted on the display screen. In this case, as shown in FIGS. 9A to 9C, if the present point D is far from the destination point A, the direction of and the distance to the destination point are briefly displayed, without displaying detailed waypoints which are not really useful for instructing the way to the destination point.

That is, in the case where the destination point is far from the present position, the number of processes for determining the present position which are performed unnecessarily quite often by the GPS processor 3 can be reduced to the minimum. Therefore, the long battery life can be expected and the position determining system can be manufactured small in size. As the present position D becomes closer to the destination point A, the position information regarding the present position is precisely and automatically acquired, resulting in displaying detailed map data. Thus, the user can obtain the distance proportion of the present position based on which the user can be acknowledged how closer he/she has approached the destination point.

In parallel with the above-described operations, as shown in FIG. 9(d), as soon as the distance from the present position D to the destination point A becomes equal to or smaller than a predetermined distance value, the reduced scale of the display screen can automatically be set large. Alternatively, as the present position D becomes closer to the destination point A, the reduced scale of the display screen can be set large either linearly or nonlinearly, enabling the navigation image to be clearly displayed.

Fourth Embodiment

The fourth embodiment of the present invention will now be explained. In this embodiment, in the position determining system having the same structure as that shown in FIG. 1A, stored in the ROM 8 are programs for executing operations which are performed by the position determining system and which are shown the flowchart in FIG. 10.

Figure 11A:
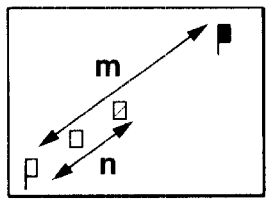
FIGS. 11A to 11C are diagrams each showing a display image for explaining the operations of the position determining system in GPS mode.

FIG. 10 shows the operations of the position determining system in GPS mode, as selected by the user. When the position determining system is in such mode, the GPS processor 3 calculates a distance proportion P of the present position with respect to the destination point on the basis of the position information (latitude/longitude) regarding the present position acquired in the previous position determination process (Step SC1). The distance proportion P of the present position represents the relationship of a distance N between the departure point and the present point to a distance M between the departure point and the destination point. Thus, the distance proportion P becomes "1", when having reached the destination point, that is, the present position coincides with the destination point (refer to FIG. 11A).

Figure 11B:
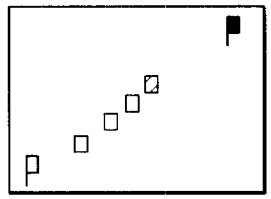

Based on the calculated distance proportion P, the GPS processor 3 calculates a time interval for position determination with using a given formula, and stores the calculated time interval in the RAM 7 as a set time interval (Step SC2). In this embodiment, the formula used for obtaining the time interval is "1/P (sec)". When the destination point is far from the present position, and the distance proportion P is as low as 1%, for example, a long time interval of 100 seconds is set. The closer the destination point, the shorter the time interval (refer to FIG. 11B). Particularly, when the present position D coincides with the destination point A, the shortest time interval of 1 second is set.

Figure 11C:
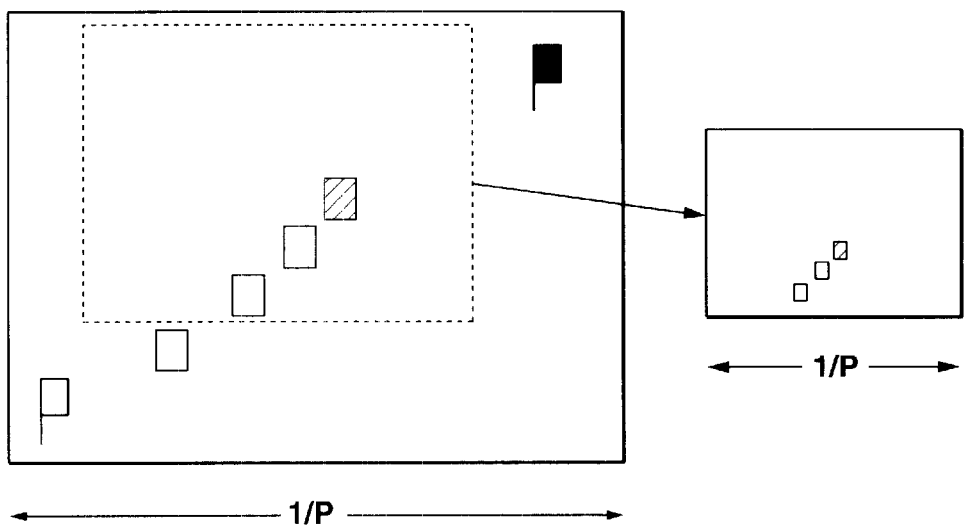

After the distance proportion P, as a display reduced scale, is stored in the RAM 7 (Step SC3), if a time period which is stored in the RAM 7 has not elapsed ("No" in Step SC4), the flow returns back to Step SC1. On the contrary, if a time period has elapsed ("Yes" in Step SC4), another position determination process is performed (Step SC5), and the display screen is set in the display reduced scale which has been stored in the RAM 7 in Step SC3 (Step SC6). The circumferential area around the present point is successively displayed in an enlarged scale (refer to FIG. 11C). Then, the flow returns to Step SC1, and the above-described procedure is repeated.

In this embodiment likewise in the third embodiment, when the destination point is far from the present position, the number of position determination processes which are performed unnecessarily quite often by the GPS processor 3 can be reduced to the minimum. Thus, the long battery life can be expected, and the position determining system can be miniaturized. As the present position D becomes closer to the destination point A, the position information regarding the present position is precisely and automatically acquired, resulting in displaying detailed map data. If such position information is displayed in detail, the user can acquire the information based on which he/she can be aware how closer he/she has approached the destination point. Since, the display reduced scale is automatically set large in proportion to the distance from the present position to the destination point, resulting in clear display of the map information.

If the display reduced scale is set large, the image representing an area around the present position can be clearly displayed on the display screen, while the distance proportion based on which the user is aware how closer he/she has approached the destination point is not easily estimated. However, by controlling the map display in the following manner, such distance proportion can be appropriately acquired even in the above-described case.

Figure 12:
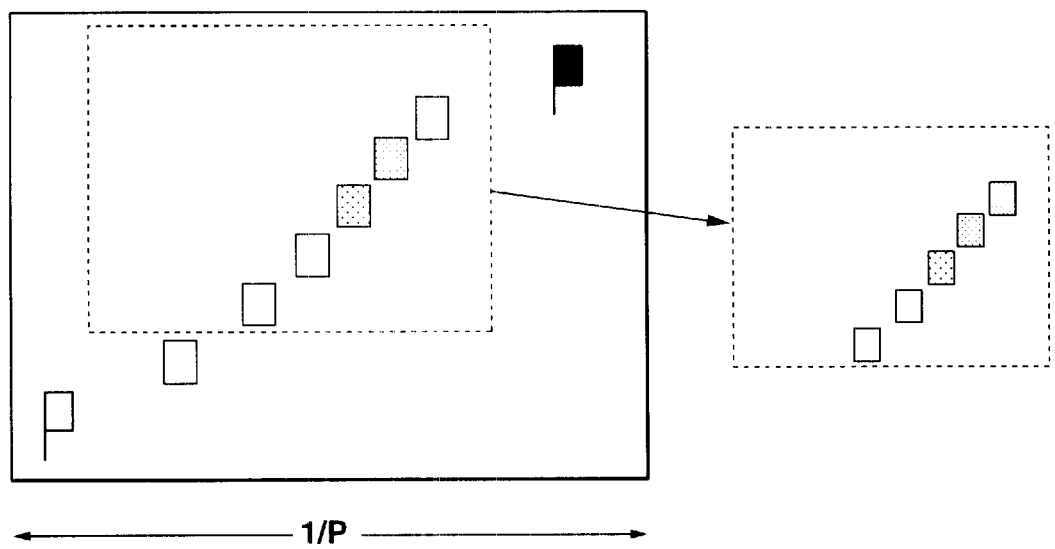
FIG. 12 is a diagram showing a display image for explaining further operations of the position determining system in GPS mode.

As shown in FIG. 12, by changing the display conditions, such as the gradation or the colors of dots, as approaching the destination point, the distance proportion with respect to the destination point can clearly be shown.

Fifth Embodiment

The fifth embodiment of the present invention will now be explained. In this embodiment, in the position determining system having the same structure as that shown in FIG. 1A, stored in the ROM 8 are data forming a time interval setting table T3, in which a plurality of travelling speeds E and time intervals D for position determination are stored in a manner corresponding with each other. To be more specific, the plurality of travelling speeds E and the time intervals D for position determination are set in such a manner that the higher the travelling speed, the shorter the time interval.

Figures 13, 14:
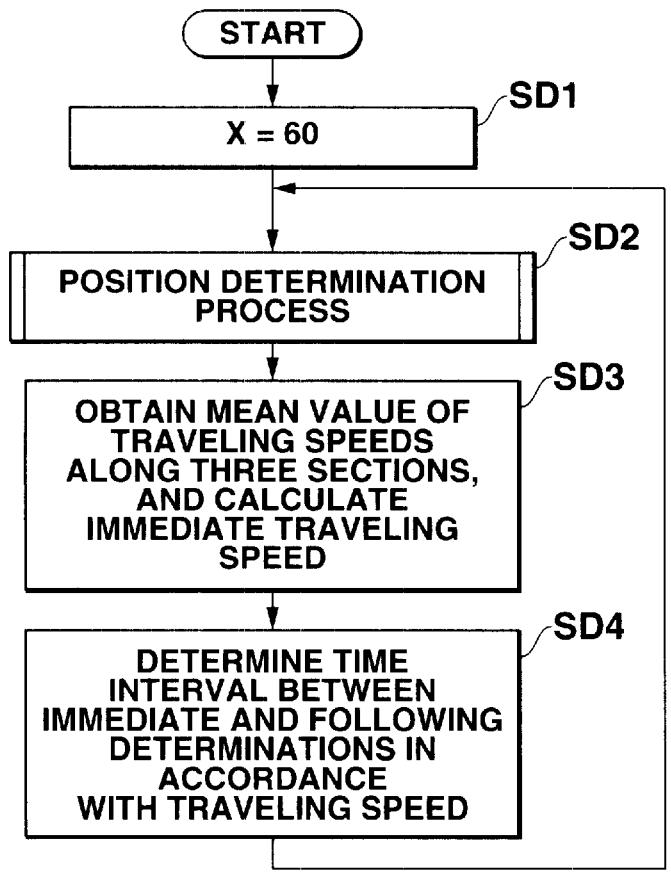
FIG. 13 is a diagram showing a time setting table according to the fifth embodiment of the present invention.
FIG. 14 is a flowchart for explaining a position determination process performed by the position determining system being in GPS mode.

In this embodiment, operations of the position determining system which is in GPS mode selected by the user will now be explained with reference to the flowchart shown in FIG. 14. When the position determining system is in GPS mode, as selected by the user, the time interval for position determination is set at an initial value of sixty seconds (Step SD1). Afterwards, the GPS processor 3 performs a position determination process for determining the position (Step SD2). The GPS processor 3 controls the display unit to display a navigation image for informing the user of the present position, and stores the time the present position has been determined in the RAM 7. The time the present position has been determined is updated, in every action of determining the position. The time data regarding the times the previous four position determinations are performed are stored in the RAM 7 at all times.

Subsequently, the mean value of the travelling speeds along three sections among the present position and the last three points, where the position determinations have been performed, is obtained based on the position information (latitude/longitude) regarding the positions of such points. On the basis of the obtained mean value and the time data stored in the RAM 7, the immediate traveling speed (the mean value of the traveling speeds) is calculated (Step SD3). The GPS processor 3 acquires from the time interval setting table T3 a time interval corresponding to the calculated traveling speed, stores the acquired data in the RAM 7. Then, the GPS processor 3 sets the acquired time interval as a period of time between the immediate determination and the following determination (Step SD4), and the flow returns back to Step SD2, in which the position determination process is performed.

In consideration of the above, in a case where the traveling speed is low, no distinctive difference is found in the positions at regular time intervals, that is, the present position coincides with the previously-determined point (no traveling is found). In such a case, the GPS processor 3 does not perform such an operation for determining the present position, thus eliminating unnecessary processes. Therefore, the long battery life can be expected, and the position determining system can be miniaturized. In this embodiment, the GPS processor 3 can advantageously save unnecessary position determination processes wherever the position is, unlike in the third and fourth embodiments.

Sixth Embodiment

The sixth embodiment of the present invention will now be described. In this embodiment, in the position determining system having the same structure as that shown in FIG. 1A, the CPU 4 checks the voltage of the battery included in the power supply circuit 6, and the ROM 8 stores programs for making the CPU 4 execute the following operations.

Figure 15:
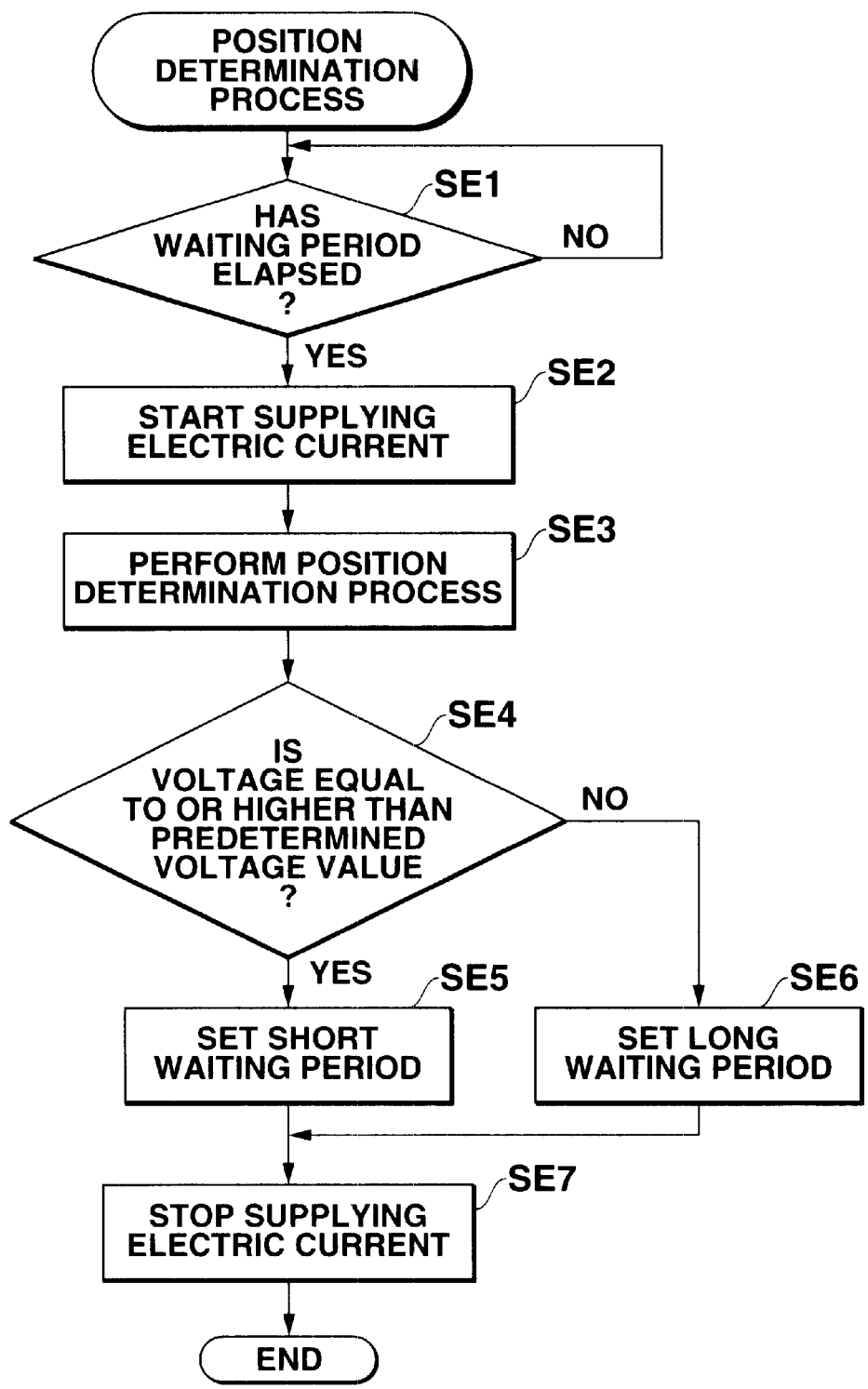
FIG. 15 is a flowchart for explaining a position determination process performed by the position determining system, in automatic position determination mode, according to the sixth embodiment of the present invention.

FIG. 15 is a flowchart for explaining a position determination process which is performed by the CPU 4 in the position determining system in automatic position-determination mode, during which the position determination is performed intermittently.

After the CPU 4 is suspended for a predetermined period of time ("Yes" in Step SE1), the CPU 4 starts supplying electric current directed from the power supply circuit 6 to the GPS processor 3 (Step SE2). The GPS processor 3 starts receiving information sent from satellites, and determines its position (Step SE3). Then, the information regarding the determined position is then sent to the CPU 4. The CPU 4 checks the voltage of the battery through the power supply circuit 6, and determines whether the voltage is equal to or higher than a predetermined voltage value (Step SE4). When determined that the voltage is lower than a predetermined voltage value, the CPU 4 sets a waiting period, which is one of waiting periods and which is shorter than the other, as the next waiting time during which the CPU 4 is suspended (Step SE5). Alternatively, when determined that the voltage is equal to or higher than a predetermined voltage value, the CPU 4 sets a waiting period, which is the other waiting period and which is longer than the other waiting period, as the next waiting time during which the CPU 4 is suspended (Step SE6). Thereafter, the CPU 4 stops supplying the electric current to the GPS processor 3 (Step SE7), and the flow ends.

When the system is running out of battery power, that is, the voltage of the battery is lower than a predetermined voltage value, supplying the electric power to the GPS processor 3 is suspended for a long period of time, and the load onto the position determining system becomes light. As a result of this, the long battery life can be expected, and the size of the position determining system can be manufactured in small size.

In this embodiment, either one of long and short waiting periods is set depending on whether the voltage of the battery is equal to or higher than a predetermined voltage value or whether the voltage is lower than a predetermined voltage value. However, three or more waiting periods can be set in accordance with the voltage of the battery. In such a case, the load on the position determining system can become light in accordance with the remaining voltage of the battery, even before the system is running out of the battery power.

Figure 16:
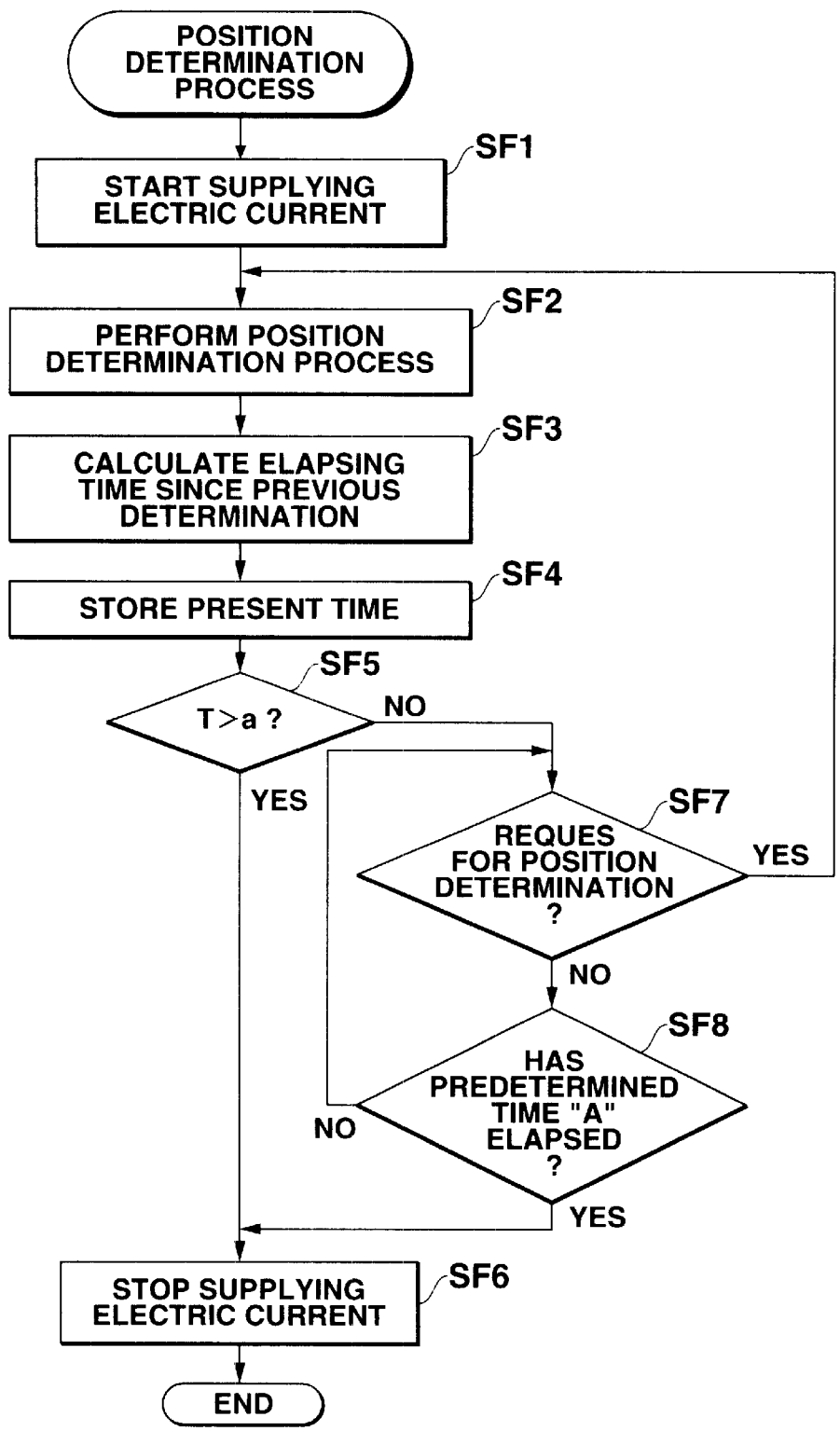
FIG. 16 is a flowchart for explaining a position determination process performed by the position determining system being in manual control mode.

FIG. 16 is a flowchart for explaining operations which are performed by the CPU 4, when the position determining system is in manual control mode, as selected by the user. When the position determining system is in such manual control mode, the CPU 4 starts supplying electric current to the GPS processor 3 (Step SF1).

Then, the GPS processor 3 starts receiving signals from satellites so as to determine its position (Step SF2), and sends the determined position to the CPU 4.

The CPU 4 calculates an elapsing time T since the last time the position determination process has been performed (Step SF3), and stores the present time in the RAM 7 (Step SF4). Subsequently, the CPU 4 determines whether the elapsing time T exceeds a predetermined period of time A which has been set in advance (Step SF5). When determined that the elapsing time T exceeds the predetermined period of time A, the CPU 4 immediately stops supplying electric current to the GPS processor 3 (Step SF6), and the position determination process ends. Alternatively, when determined that the elapsing time T is equal to or shorter than the predetermined period of time A ("No" in Step SF5), the CPU 4 waits for a request sent from the user requesting for position determination, during the time the predetermined period of time A elapses ("No" in Step SF8). When the CPU 4 receives a request from the user requesting for position determination, during such time ("Yes" in Step SF7), the flow returns back to Step SF2, and the CPU 4 controls the GPS processor 3 to perform another position determination process.

Alternatively, if the CPU 4 does not receive such a request from the user, during the time the predetermined period of time A elapses ("Yes" in Step SF8), it stops supplying the electric current to the GPS processor 3 (Step SF6), and the flow ends.

In the above-described manner, the GPS processor 3 can save electric power which is not necessary during the time the position determination process is not performed. This realizes that the battery have longer life, and the position determining system can be miniaturized in size.

During the predetermined period of time A, the GPS processor 3 continues to be activated, that is, the electric current is supplied thereto, and it can continuously receive the signals from the satellites. This makes possible eliminating the time needed for the next position determination process. Furthermore, the long battery life can be expected, and the position determining system of this invention can be manufactured in small size.

Seventh Embodiment

The seventh embodiment of the present invention will now be explained. In this embodiment, in the position determining system having the same structure as that shown in FIG. 1A, stored in the ROM 8 are programs for making the CPU 4 execute the following operations.

Figure 17:
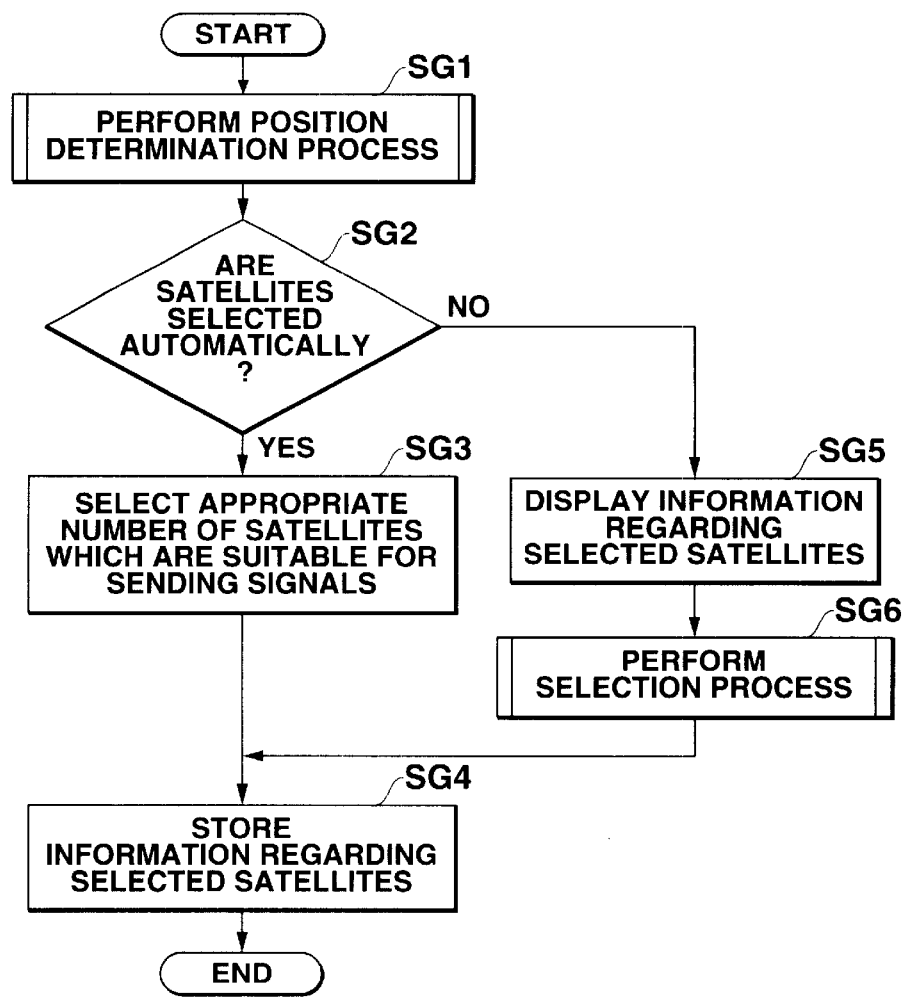
FIG. 17 is a flowchart for explaining a position determination process performed by the process determining system, being in satellite channel setting mode, according to the seventh embodiment of the present invention.

FIG. 17 is a flowchart for explaining a position determination process which is performed by the position determining system in satellite channel setting mode, as selected by the user. In the position determining system, in such mode, in this embodiment, the GPS processor 3 performs a position determination process, by acquiring position information (latitude/longitude) regarding the present position thereof (Step SG1).

The GPS processor 3 waits for the user selecting whether to select satellites automatically or manually. When selected that the satellites are to be selected automatically ("Yes" in Step SG2), the GPS processor selects an appropriate number of satellites, from which signals can be sent for a long period of time and which are suitable for the position determining system to receive such signals in the present position (Step SG3). In this embodiment, it is assumed that four satellites are so selected that the position of the position determining system is determined in three dimensions. The information regarding the selected satellites is stored and set in the RAM 7 (Step SG4), then the position determination process ends.

If the selection made in Step SG2 is "No", that is, when selected that the satellites are to be selected manually, the GPS processor 3 displays the information regarding the satellites from which signals are sent during the position determination process, as processed in Step SG1, and selection auxiliary information on the display unit (Step SG5). Such selection auxiliary information represents in which direction the respective satellites are positioned with respect to the present position of the position determining system, for example. In this case, when the user is positioned between the position determining system and a certain satellite, electric waves from the satellite are interrupted from being sent to the system. In such a case, another satellite from which electric waves are preferably sent to the system can be selected.

After performing a selection process in which a desired number of satellites (three or more) are selected and one of the already-selected satellites is changed to another (Step SG6), the CPU 4 stores and sets the information regarding the selected satellites in a predetermined storage area of the RAM 7 (Step SG4), then the flow ends.

Figure 18:
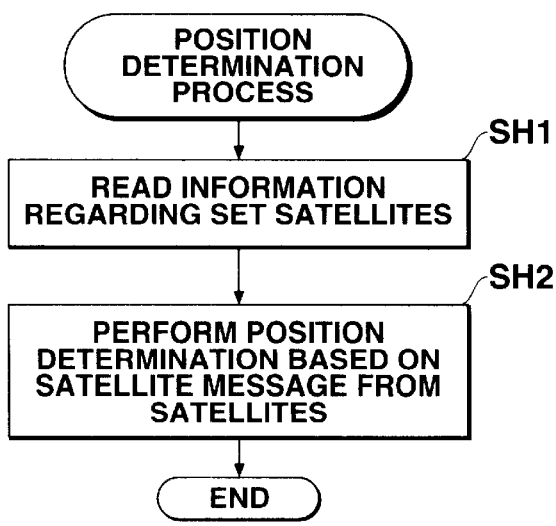
FIG. 18 is a flowchart for explaining a position determination process performed by the process determining system.

In the position determining system according to this embodiment, after performing the process for selecting the satellites used in satellite channel setting mode, the CPU 4 executes another position determining process which is described in the flowchart of FIG. 18.

When the process begins, the CPU 4 reads out information regarding the set GPS satellites from the RAM 7 (Step SH1), and performs a position determination process based on a satellite message sent from the plurality of GPS satellites (Step SH2), and the flow ends.

Accordingly, in the position determination process, a predetermined number of satellites are required for obtaining the position information, resulting in eliminating the time needed for securing any other satellite(s). Thus, it becomes possible to save the electric power consumed during such a process, thereby the long battery life can be expected, and the position determining system can be miniaturized in size. In this embodiment, since the satellites to be secured are determined in accordance with the present position or the usage conditions of the user, the information from the secured satellites can certainly and advantageously be transmitted to the system.

Unlike in this embodiment, in a case where a required number of satellites which are used for the position determination is determined, a process, in which securing further satellites is terminated, is performed at the point where the determined number of satellites are secured.

In a case where a large number of satellites used for position determination are set, the improvement in the accuracy of the position determination can be realized. As the present position becomes closer to the destination point, a larger number of satellites used for determining the position can be set. In such a case, the GPS processor 3 can save the electric power in the position determination process which is not necessarily performed with high accuracy.

Another Embodiment

Another embodiment besides the above-described embodiments will now be explained. In the position determining system in this embodiment, likewise the above embodiments, the long battery life can be expected, and the position determining system can be manufactured in small size.

In the position determining system having the same structure as that shown in FIG. 1A, when the display reduced scale is set in a predetermined value or the present position approaches the destination point at a predetermined distance away therefrom, the CPU 4 controls the direction detecting section 12 or the altitude detecting section 13 to calculate the absolute direction or the absolute altitude of the position determining system, thereby displaying the calculated results together with the navigation image on the display unit. As a result of this, the position of the position determining system can be obtained with high accuracy, as needed, and the GPS processor 4 can save the electric power in determining the position of the position determining system with low accuracy.

In the position determining system having the same structure as that shown in FIG. 1A, the satellite data storage section 10 stores calculated data regarding leap seconds and needed when correcting the satellite time sent from the GPS satellites when determining the position. Based on the calculated data, the CPU 4 performs a process for correcting the error in the satellite time and easily determining the present time. Thereby, the GPS processor 3 is not required to receive data regarding the leap seconds. That is, it is not required for the GPS processor 3 to receive almanac data which include data regarding the leap seconds and which are transmitted from the GPS processor at intervals of 12.5 minutes, thereby saving the electric power. In this embodiment, the data regarding the leap seconds irregularly vary in value. Even while determining the position of the position determining system, the present position can be determined with high accuracy as long as the updated calculated data stored in the satellite data storage section 10 is used.

Each of the so-far-described embodiments according to this invention may not only be solely realized, but also be combined with another, thereby remarkable advantages of the present invention can be expected.

The position display device is not limited to a dedicated system, and can be realized using an ordinary computer system. For example, the position determining system which execute the above-described processes, can be realized installing programs for carrying out the above-described processes into computers including GPS units.

The medium for supplying the programs to computers may be a communications medium (a medium which temporarily in a fluid manner retains the programs, like a communications line, a communication network and a communication system). For example, the programs may be presented on the BBS (Bulletin Board system) of the communications network and may be supplied to the computers via the network.

The position determining system which executes the above-described processes can be realized, by presenting the programs on the BBS of the communication network, and by executing the programs on computers, which has received signals embodied in a carrier wave and representing instruction sequences forming such programs.

Various embodiments and changes may be made thereunto without departing from the broad spirit and scope of the invention. The above-described embodiments are intended to illustrate the present invention, not to limit the scope of the present invention. The scope of the present invention is shown by the attached claims rather than the embodiments. Various modifications made within the meaning of an equivalent of the claims of the invention and within the claims are to be regarded to be in the scope of the present invention.

This application is based on Japanese Patent Application No. H10-377621 filed on Dec. 31, 1998 and including specification, claims, drawings and summary. The disclosure of the above Japanese Patent Application is incorporated herein by reference in its entirety.

What is claimed is:

1. A portable battery driven position determining system comprising:
   a receiver which receives position information sent from GPS satellites;
   a position determining unit which determines a position of the receiver based on the position information received by the receiver;
   a display unit which displays the position of the receiver which is determined by the position determining unit;
   a setting table which sets a time interval at which the position of the receiver is determined in correspondence with a display reduced scale of the display unit; and
   a controller which controls the time interval to be shortened as the display reduced scale becomes smaller, based on the setting table.

2. A position determining system comprising:
   a receiver which receives position information sent from GPS satellites;
   a position determining unit which determines a position of the receiver based on the position information received by the receiver; and
   a controller which detects a voltage of a power source which supplies electrical power to said system, determines whether the detected voltage is equal to or greater than a predetermined voltage, and sets a time interval at which the position determining unit determines the position of the receiver based on whether the detected voltage is equal to or greater than the predetermined voltage.

3. The position determining system according to claim 2, wherein said controller detects a voltage of the power source, and sets the interval at which the position determining unit determines the position of the receiver based on whether the detected voltage is equal to or greater than a predetermined voltage.

4. A portable battery driven position determining system comprising:
   a receiver which receives position information sent from a plurality of GPS satellites;
   a position determining unit which determines a position of the receiver based on the position information received by the receiver; and
   a controller which controls a time interval at which the position of the receiver is determined by the position determining unit based on a distance between a present position of the receiver and a destination point, in a manner to shorten the time interval as the distance between the present position of the receiver and the destination point becomes shorter.

5. A portable battery driven position determining system comprising:
   a receiver which receives position information sent from a plurality of GPS satellites;
   a position determining unit which determines a position of the receiver based on the position information received by the receiver;
   a calculation unit which calculates a traveling speed of the system based on a distance between a plurality of determined positions including the position of the receiver determined by the position determining unit and time points at which the positions are determined; and
   a controller which controls a time interval at which the position of the receiver is determined to be shortened, as the traveling speed calculated by the calculation unit becomes higher.

6. A method of operating of a portable battery driven position determining system which comprises a receiver, a position determining unit, a display unit, a setting table and a controller, said method comprising:
   operating the receiver to receive position information sent from GPS satellites;
   operating the position determining unit to determine a position of the receiver based on the position information received by the receiver;
   operating the display unit to display the position of the receiver which is determined by the position determining unit;
   utilizing the setting table to set a time interval at which the position of the receiver is determined in correspondence with a display reduced scale of the display unit; and
   operating the controller to control the time interval to be shortened as the display reduced scale becomes smaller, based on the setting table.

7. A method of operating of a position determining system which comprises a receiver, a position determining unit, and a controller, said method comprising:
   operating the receiver to receive position information sent from GPS satellites;
   operating the position determining unit to determine a position of the receiver based on the position information received by the receiver; and
   operating the controller to detect a voltage of a power source which supplies electrical power to said system, determine whether the detected voltage is equal to or greater than a predetermined voltage, and set a time interval at which the position determining unit determines the position of the receiver based on whether the detected voltage is equal to or greater than the predetermined voltage.

8. A method of operating of a portable battery driven position determining system which comprises a receiver, a position determining unit, and a controller, said method comprising:
   operating the receiver to receive position information sent from a plurality of GPS satellites;

operating the position determining unit to determine a position of the receiver based on the position information received by the receiver; and operating the controller to control a time interval at which the position of the receiver is determined by the position determining unit based on a distance between a present position of the receiver and a destination point, in a manner to shorten the time interval as the distance between the present position of the receiver and the destination point becomes shorter.

9. A method of operating of a portable battery driven position determining system which comprises a receiver, a position determining unit, a calculation unit and a controller, said method comprising:

operating the receiver to receive position information sent from a plurality of GPS satellites;

operating the position determining unit to determine a position of the receiver based on the position information received by the receiver;

operating the calculation unit to calculate a traveling speed of the system based on a distance between a plurality of determined positions including the position of the receiver determined by the position determining unit and time points at which the positions are determined; and operating the controller to control a time interval at which the position of the receiver is determined to be shortened, as the traveling speed calculated by the calculation unit becomes higher.

10. A computer program for controlling a portable battery driven position determining system, wherein said position determining system comprises a receiver, a position determining unit, a display unit, a setting table, and a controller, said computer program comprising:

code for causing the receiver to receive position information sent from GPS satellites;

code for causing the position determining unit to determine a position of the receiver based on the position information received by the receiver;

code for causing the display unit to display the position of the receiver which is determined by the position determining unit;

code for causing the setting table to set a time interval at which the position of the receiver is determined in correspondence with a display reduced scale of the display unit; and code for causing the controller to control the time interval to be shortened as the display reduced scale becomes smaller, based on the setting table.

11. A computer program for controlling a position determining system, wherein said position determining system comprises a receiver, a position determining unit, and a controller, said computer program comprising:

code for causing the receiver to receive position information sent from GPS satellites;

code for causing the position determining unit to determine a position of the receiver based on the position information received by the receiver; and code for causing the controller to detect a voltage of a power source which supplies electrical power to said system, determine whether the detected voltage is equal to or greater than a predetermined voltage, and set a time interval at which the position determining unit determines the position of the receiver based on whether the detected voltage is equal to or greater than the predetermined voltage.

12. A computer program for controlling a portable battery driven position determining system, wherein said position determining system comprises a receiver, a position determining unit, and a controller, said computer program comprising:

code for causing the receiver to receive position information sent from a plurality of GPS satellites;

code for causing the position determining unit to determine a position of the receiver based on the position information received by the receiver; and code for causing the controller to control a time interval at which the position of the receiver is determined by the position determining unit based on a distance between a present position of the receiver and a destination point, in a manner to shorten the time interval as the distance between the present position of the receiver and the destination point becomes shorter.

13. A computer program for controlling a portable battery driven position determining system, wherein said position determining system comprises a receiver, a position determining unit, a calculation unit, and a controller, said computer program comprising:

code for causing the receiver to receive position information sent from a plurality of GPS satellites;

code for causing the position determining unit to determine a position of the receiver based on the position information received by the receiver;

code for causing the calculation unit to calculate a traveling speed of the system based on a distance between a plurality of determined positions including the position of the receiver determined by the position determining unit and time points at which the positions are determined; and code for causing the controller to control a time interval at which the position of the receiver is determined to be shortened, as the traveling speed calculated by the calculation unit becomes higher.

* * * * *